United States Patent
Zubry

(10) Patent No.: US 7,255,684 B2
(45) Date of Patent: Aug. 14, 2007

(54) MEDICAL INJECTION SYSTEM

(76) Inventor: Boris Zubry, 12 E. Countryside Dr., Princeton, NJ (US) 08540

( * ) Notice: Subject to any disclaimer, the term of this patent is extended or adjusted under 35 U.S.C. 154(b) by 53 days.

(21) Appl. No.: 11/199,113

(22) Filed: Aug. 8, 2005

(65) Prior Publication Data

US 2006/0030816 A1 Feb. 9, 2006

Related U.S. Application Data

(60) Provisional application No. 60/599,843, filed on Aug. 9, 2004.

(51) Int. Cl.
*A61M 37/00* (2006.01)
*A61M 5/00* (2006.01)
*A61M 31/00* (2006.01)

(52) U.S. Cl. ............ 604/131; 604/187; 604/232; 604/500

(58) Field of Classification Search ............ 604/61, 604/131, 152, 187, 200, 201, 218, 228, 232, 604/233, 234, 235, 500, 506, 519
See application file for complete search history.

(56) References Cited

U.S. PATENT DOCUMENTS

| | | | |
|---|---|---|---|
| 2,825,332 A | 3/1958 | Johnson | |
| 3,051,173 A | 8/1962 | Johnson et al. | |
| 3,136,313 A | 6/1964 | Enstrom et al. | |
| 3,964,481 A | 6/1976 | Gourlandt et al. | |
| 3,977,402 A | 8/1976 | Pike | |
| 4,108,177 A * | 8/1978 | Pistor | 604/155 |
| 4,435,173 A | 3/1984 | Siposs et al. | |
| 4,610,658 A * | 9/1986 | Buchwald et al. | 604/9 |
| 4,662,872 A | 5/1987 | Cane | |
| 5,505,706 A | 4/1996 | Maus et al. | |
| 6,056,716 A | 5/2000 | D'Antonio et al. | |
| 6,537,268 B1 | 3/2003 | Gibson et al. | |
| 6,752,789 B2 * | 6/2004 | Duchon et al. | 604/228 |
| 2002/0183616 A1 | 12/2002 | Toews et al. | |
| 2003/0040715 A1 * | 2/2003 | D'Antonio et al. | 604/187 |
| 2003/0144634 A1 * | 7/2003 | Langley et al. | 604/232 |
| 2004/0030298 A1 | 2/2004 | Veasey et al. | |

OTHER PUBLICATIONS

International Search Report for PCT Application No. PCT/US05/28216 issued by ISA/US on Dec. 23, 2005.
Title: Plungerless Syringe, Author: Boris Zubry, Distributed: Nov. 2002.
Supporting Online Material for Catalytic Reduction of Dinitrogen to Ammonia at a Single Molybdenum Center; http://www.sciencemag.org/cgi/data/301/5629/76/DC1/1; by Dmitry V. Yandulov, Richard R. Schrock Contribution from Department of Chemistry Massachusetts Institute of Technology Cambridge, MA 02139; Published on or before Jan. 26, 2004.

* cited by examiner

*Primary Examiner*—Kevin C. Sirmons
*Assistant Examiner*—Bhisma Mehta

(57) ABSTRACT

A method and apparatus for the storage and transfer of medical material includes a syringe having a rodless piston magnetically coupled to an actuator that is positioned along the syringe independent of the rodless piston. The syringe may also include a medical material stored in a cartridge.

9 Claims, 5 Drawing Sheets

MEDICAL INJECTION SYSTEM

CROSS-REFERENCE TO RELATED APPLICATION

This application claims the benefit of U.S. Provisional Application Ser. No. 60/599,843 filed on Aug. 9, 2004, which is incorporated herein by reference.

BACKGROUND

1. Field of the Invention

The present invention is directed to an apparatus and method for use in medical injection technology. More particularly, the present invention is directed to improved hypodermic syringe assemblies and methods for using the same.

2. Description of the Related Art

For generations, people all over the world have received injections (or fluid withdrawals) utilizing a piston driven device commonly referred to as a hypodermic syringe. Hypodermic syringe designs have not really changed much since their first inception in which a plunger formed from a piston and piston rod is manually operated to drive fluid, from a cylindrical chamber in the syringe into, or out of, a living body through a needle.

Similarly, unchanged is the way that a dosage of medicine is stored such as in an ampoule or a vial in which the period of drug shelf life is limited only by the drug stability and/or by opening of the storage vessel and introducing air and other impurities therein. One change has been in the form of a pre-filled and/or cartridge syringe in which a cylindrical drug chamber is pre-filled with a drug and sealed with a piston with an opening to receive a piston rod from the syringe at one end. However, the drug shelf life is limited by the quality of the fill and the seal between the piston and the wall of the cartridge in the opening left for the piston rod to connect with the piston.

Except in the instance of current cartridge designs, the present technological method for injecting drugs includes filling of ampoules and vials in order to store the drug for a period of time and then filling of the syringes, when needed, from these ampoules and vials. Filling of ampoules and vials is the most labor intensive and, therefore, the most expensive part of the process. In order to fill ampoules and the vials, the pharmaceutical company has to set up the cleanroom operations, purchase and set up specific equipment, maintain supply of ampoules and the vials, employ operators, administration, technicians, engineers, quality control and the quality assurance personnel dedicated to this process. Ampoules and vials have to be stored and, therefore, the warehouse space is required. Inspections, handling and shipping add to the cost of the final product by adding the manpower required to handle all these operations, rejects and damages, and the cost of extra storage, logistics and the shipping containers. And, in addition to all that, the syringes are needed to inject the drug.

Some of these issues have been addressed with pre-filled syringes. The pre-filled syringes do not need ampoules and vials, but are not very popular and common. The presently available pre-filled syringes cannot maintain sterility for a long time and, therefore, have a very short shelf life. The shelf life of the modern common pre-filled syringes is a couple of months if that much. The reason for that is that the syringe is not perfectly sealed and air, germs and bacteria can work itself in while the drug can leak out. Plastic is not an ideal material to store some of the drugs for an extended period of time. The extended plunger of the pre-filled syringe could be accidentally pushed in or pulled out changing the volume of the drug inside or letting the air in. Pre-filled syringes cannot be shipped far unless specially designed containers are used (expensive). Therefore, pre-filling has to be done locally by qualified personnel just before the distribution. This option requires the qualified personnel and the necessary equipment to be present and one still cannot store it for any extensive period of time. Therefore, it cannot be pre-filled in advance at a medical production facility adding to the high cost of shipping.

All above adds to the logistics and the expense of the drug manufacturing process. Such shortcomings are even more appreciated when considering situations such as mass vaccinations, personal insulin injections, on-location pain relievers for the military, in sporting events and remote areas. A storage vessel easily convertible into a syringe without the shortcomings discussed above would solve these problems.

Thus, the need exists for a way to provide a storage vessel that easily converts into a syringe.

SUMMARY OF THE INVENTION

The present invention includes a syringe having walls forming a cylindrical chamber. A transfer device is connected to at least one of the walls with a piston operating in the cylindrical chamber to transfer material between the transfer device and the cylindrical chamber. An actuator is magnetically coupled to the piston through at least one of the walls and is located in a position on the syringe independent of the position of the piston.

The present invention further includes a medical material storage and delivery cartridge having a casing forming a cylindrical chamber having an opening. A stopper is positioned in a sealing engagement to the casing to block the opening and is penetrable by a transfer device. A piston operates in the cylindrical chamber such that when the cartridge is connected to the transfer device, the piston transfers material between the transfer device and the cylindrical chamber.

The cartridge when transitioning between its role for storage and for delivery permits the creation of a second opening to facilitate movement of the piston during delivery.

The present invention also includes a syringe assembly using the cartridge in combination with a delivery device including a cartridge nest to hold the cartridge. A transfer interface is positioned along the cartridge nest proximate to where the stopper is held to position a transfer device in penetrating engagement with the stopper. A guard having a tensioning member is positioned along the cartridge nest to securely hold the cartridge in the nest. A magnet assembly operates along the cartridge nest to create a movable magnetic field through said casing and along with an actuator responsively coupled to the magnet assembly to moves the piston through the chamber.

The present invention includes a method as well for storing and dispensing medical material including the steps of:

providing a cartridge including a casing forming a cylindrical chamber having an opening; a stopper positioned in a sealing engagement to the casing to block the opening and penetrable by a transfer device; and a rodless piston;

inserting a medical material into the cartridge;

storing the medical material in the cartridge;

dispensing the medical material from the cartridge to a living body by operating the rodless piston in the cylindrical chamber such that when the cartridge is connected to the transfer device, the rodless piston transfers material through the transfer device from the cylindrical chamber to the living body.

BRIEF DESCRIPTION OF THE DRAWINGS

Other aspects, advantages and novel features of the invention will become more apparent from the following detailed description of the invention when considered in conjunction with the accompanying drawings wherein.

DETAILED DESCRIPTION

Figure 1:
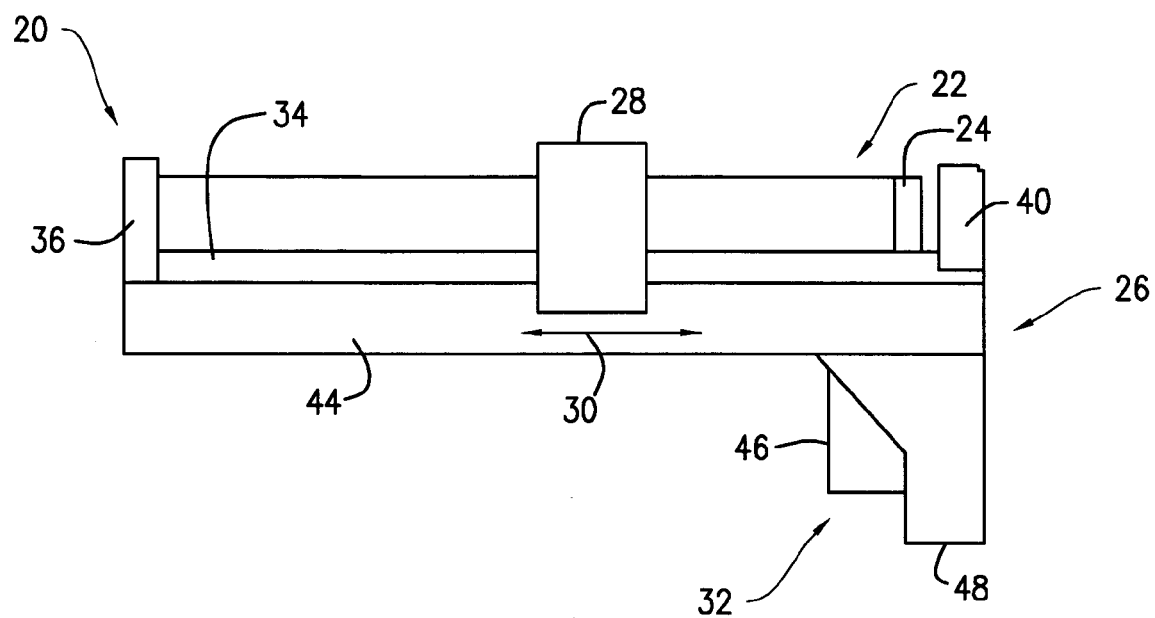
FIG. 1 is a side view of an exemplary syringe assembly in accordance with some aspects of the invention.

With reference to the drawings for purposes of illustration, the present invention is embodied in a hypodermic syringe assembly 20 (FIG. 1) that includes a cartridge 22 hollow to form a cylindrical storage chamber 23 (FIG. 2) and a piston 24 moveable within the chamber 23 to cause the withdrawal or retrieval of viscous or gaseous medical material within the chamber. The cartridge 22 is disposed for activation of the piston 24 in a delivery device 26 having a magnet assembly 28 moveably attached to the delivery device 26 to move in the direction indicated by line 30 and controlled by an actuator 32. Advantageously, the cartridge piston 24 is magnetically coupled to the magnet assembly 28 and is moveably responsive to the magnet assembly 28 for travel within the chamber 23 in the direction indicated by line 30.

It will be appreciated that this configuration thus eliminates the need for a piston rod as featured in conventional, manually operated syringes that utilize a plunger formed from a piston and piston rod.

Figure 2:
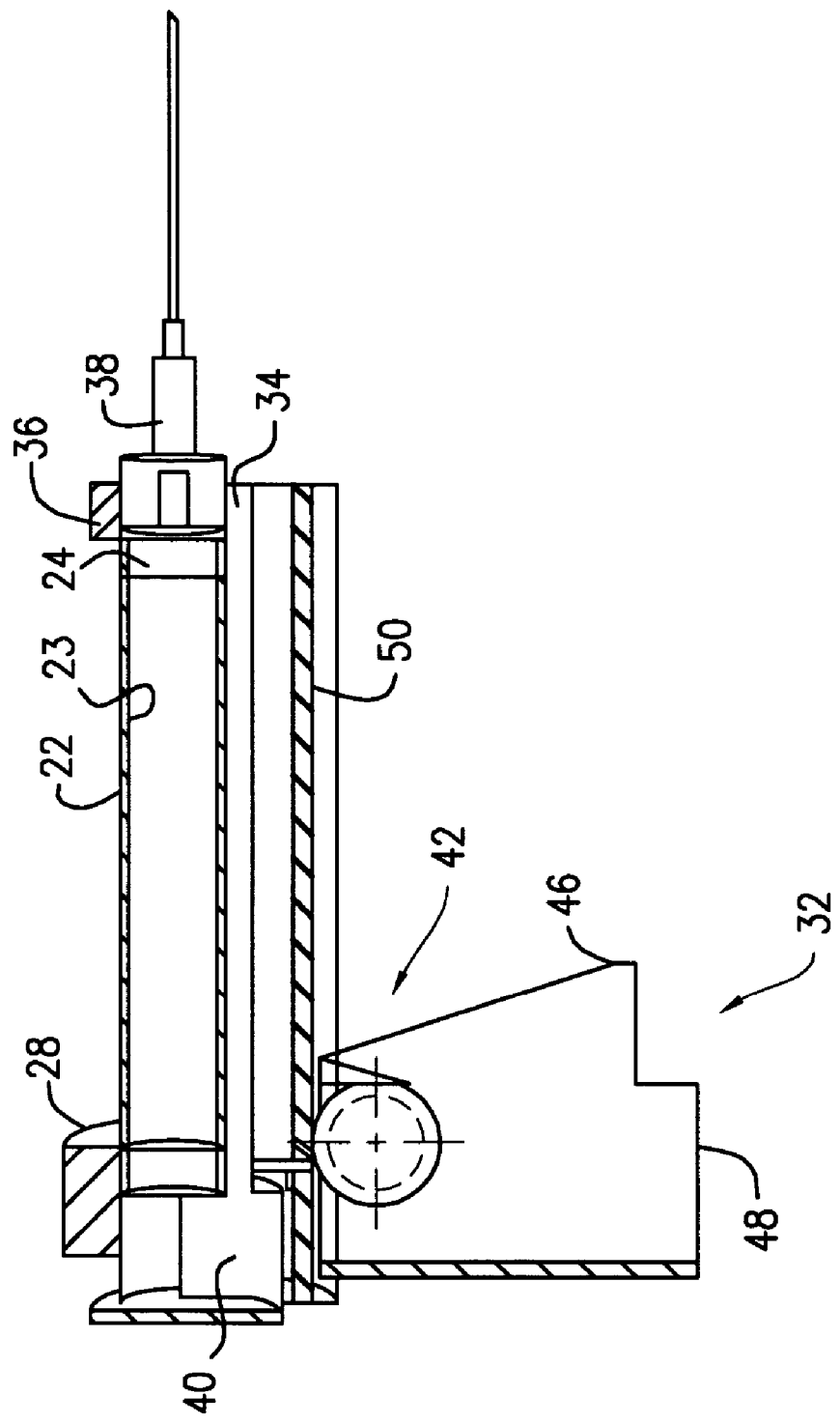
FIG. 2 is a cross-sectional view of the exemplary syringe assembly of FIG. 1.

The delivery device 26 includes a cartridge nest 34 for securely holding the cartridge 22 when in use. The cartridge nest 34 is further defined by a material transfer interface 36 that allows for attachment of the cartridge to a transfer device 38 (FIG. 2). A transfer device 38 of the type suitable for this purpose, but without limitation, is a hypodermic needle, tube, nipple or the like. An adjustable guard 40 or tensioning member secures the cartridge 22 within the cartridge nest 34 against the transfer interface 36. The guard 40 may incorporate tensioning means for holding the cartridge 22 in place against the transfer interface 36. Tensioning means of the type suitable for this purpose may include, but is not limited to, a spring, rubber or elastomeric material. The guard 40 is preferably adjustable in the direction indicated by line 30 to accommodate different lengths of cartridges 22; however, other embodiments may include a stationary guard in which the cartridges are of uniform size or the different lengths can be maintained by the tensioning means. An actuator drive train 42 (FIG. 2) that connects the actuator 32 to the moveable magnet assembly 28 is shown for exemplary purposes within a housing 44 below the cartridge nest 34. The actuator drive train 42 (FIG. 2) may be configured in any form to accommodate manual movement by an individual into a linear transfer of the magnet assembly 28 along the length of the cartridge nest 34. For exemplary, purposes the delivery device 26 is shaped as a gun with the actuator 32 forming a pivotally movable trigger 46 and grip 48 alongside the cartridge nest 34. The trigger 46 is preferably spring biased away from the grip 48 and geared when pulled toward the grip 48 to rotate a rod slotted as a screw drive 50. The magnet assembly 28 is coupled conventionally to the slots that are carved to enable the magnet assembly 28 to move linearly in both directions. To facilitate usage, the trigger 46 is preferably calibrated with the screw drive 50 such that one pull of the trigger 46 causes the magnet assembly 28 to move the complete length of a path along the cartridge nest length. This eliminates the need to "pump" the trigger multiple times to move the magnet assembly completely in one direction. This allows for in mass vaccination situations for the delivery device to be operated quickly and reloaded with new needles and cartridges for repeated use. The delivery device housing 44 and drive train 42 may be manufactured from plastic or metal as required for intended use, manufacturing cost and durability.

The magnet assembly 28, sized and shaped to surround the cartridge 22 with a magnetic field and attach to the actuator drive train 42, includes a magnetic field, formed from one or more magnets, sufficient to move the magnetically responsive piston 24 when aligned with the piston 24 within the cartridge 22 along the length of the cartridge chamber 23. Factors to consider when selecting the magnetic field strength of the magnet assembly include the thickness of the cartridge wall, material used for cartridge manufacturing, magnets, materials used for the piston, friction between the wall and the piston inside the cartridge chamber, resistance of the body to injection within tissue and veins from blood pressure, relevant pharmaceutical requirements and the viscosity of the medical material to be transferred. For purposes of this invention medical material may include, but is not limited to, gas, powder or liquid material or other material typically delivered to or withdrawn from a living body. Furthermore the term "medical material" is used to promote and facilitate understanding of the invention's operation in terms of conventional syringe uses, but is not intended to be limiting and can refer to any chemical material or be used in applications not associated with a living body.

It will be appreciated that the plunger-less design of the present invention allows for the placement of the manual actuator to be located alongside the chamber or in another location more appropriate for the ergonomic design and handling of the device rather than rearward of the storage chamber as required by mechanical requirements when working with a plunger drive mechanism. Furthermore, the overall size of the delivery device can be adapted to be more compact without the need to accommodate a withdrawn plunger rod.

Figure 3:
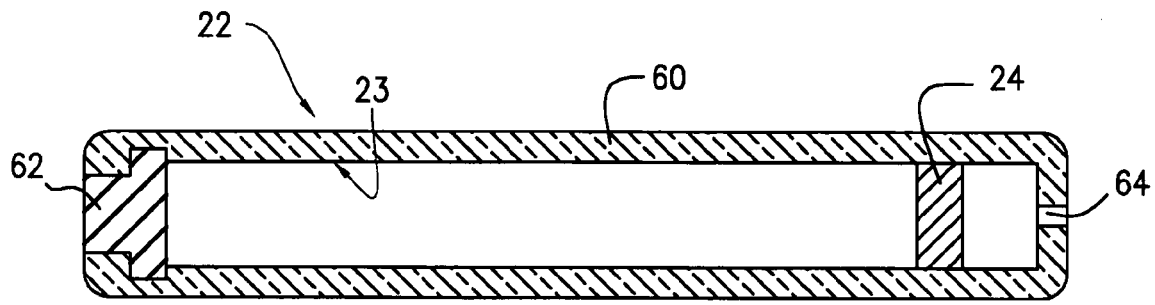
FIG. 3 is a cross-sectional side view of an exemplary cartridge of FIG. 1 having a second appearance in accordance with some aspects of the invention.

With reference now to FIG. 3, an exemplary cartridge 22 generally includes a cylindrical casing 60 made of conventional materials for storing medical material and depending upon the application may include, but is not limited to, glass, plastic, ceramic or metal. The cartridge chamber 23 formed by the casing includes a magnetically responsive piston 24 sized and shaped to move easily through the chamber 23 while providing a sufficient seal between the piston 24 and cartridge casing 60 to inhale or expel medical material when coupled with a transfer device without allowing the medical material to pass to the other side of the piston 24. The piston 24 may include any magnetically responsive material or may be magnetic itself depending upon the application. Furthermore, in instances where the medical material is reactive to the piston material, the piston may be coated with a cover material that is inert to or non-reactive with the medical material. A rubber stopper 62 is provided to secure the medical material in the chamber, but may be penetrated with sufficient ease to permit connection to a transfer device when connected to a transfer interface within a delivery device. An air evacuation slot 64 is provided in the casing to allow for ambient air to fill or expel from the empty portion of the cartridge chamber 23. While enlarged in the drawing for purposes of illustration, it will be appreciated by those skilled in the art that the air slot diameter need only be large enough to permit the free flow of air when the piston 24 is moved. Unlike conventional syringe cartridges that are designed to accommodate contact of a piston rod with the piston, the air slot of the present invention can easily be covered and sealed to prevent exposure of medical material with ambient air thereby increasing the shelf life capability of the cartridge.

Figure 4:
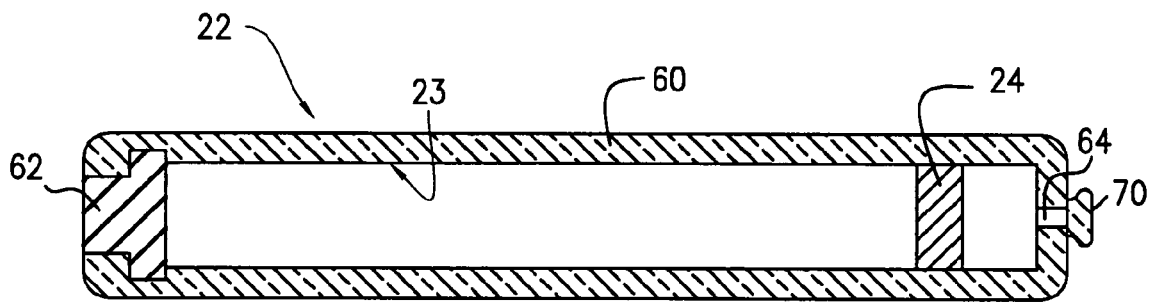
FIG. 4 is a cross-sectional side view of an exemplary cartridge of FIG. 1 having an alternate appearance in accordance with some aspects of the invention.

With reference to FIG. 4 where like reference numerals refer to like structures, an exemplary cartridge design for extended storage is shown wherein the cartridge 22 includes a knob 70 or ball of excess casing material covering the air slot 64. Where the casing 60 is manufactured from glass, plastic, ceramic or the like, a break-away or cutaway knob 70 or ball made of like casing material or material that readily adheres to the casing material is provided to seal the air slot 64. When the cartridge 22 is selected for use to dispense the medicine, the knob 70 or ball of material is broken or cut away from the hole. It will be appreciated by those skilled in the art that the guard 40 (FIGS. 1 and 2) of the dispensing device 26 may be adapted with a sharp edge that that upon insertion of the cartridge 22 (FIG. 4) into the dispensing device, the knob 70 is pressed against the guard and is broken or cut off of the casing 60.

Figure 5:
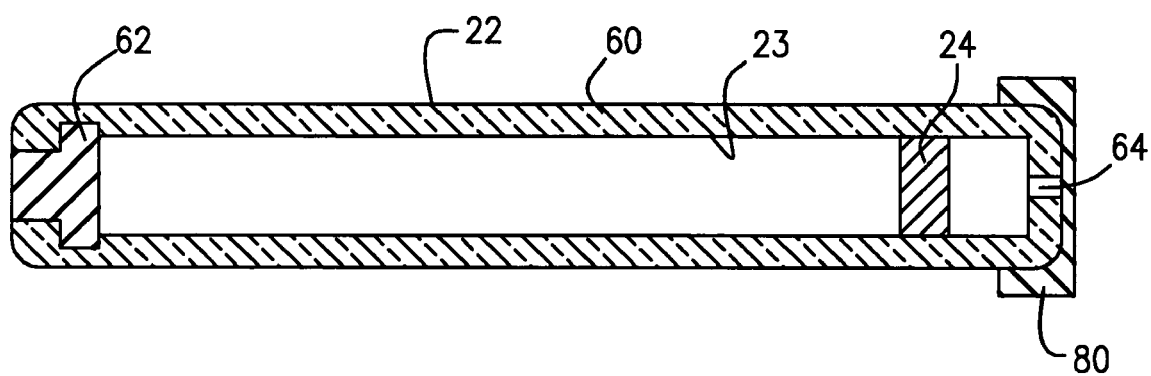
FIG. 5 is a cross-sectional side view of an exemplary cartridge of FIG. 1 having another appearance in accordance with some aspects of the invention.

With reference now to FIG. 5 where like reference numerals refer to like structures, an exemplary cartridge design for extended storage is shown wherein the cartridge 22 includes a cap 80 sealing engaged over the end of the cartridge 22 with the air slot 64. This embodiment provides extended shelf life for the medical material with more options for use than in FIG. 4, as the cap 80 can be used with cartridges intended for the dispensing of drugs as well as cartridges intended for the withdraw of samples from a living body. Those skilled in the art will appreciate that the increased contact surface area of the cap 80 with the casing 60 about the air slot 64 provides a better sealing engagement than can be obtained with conventional syringe cartridges.

Figure 6:
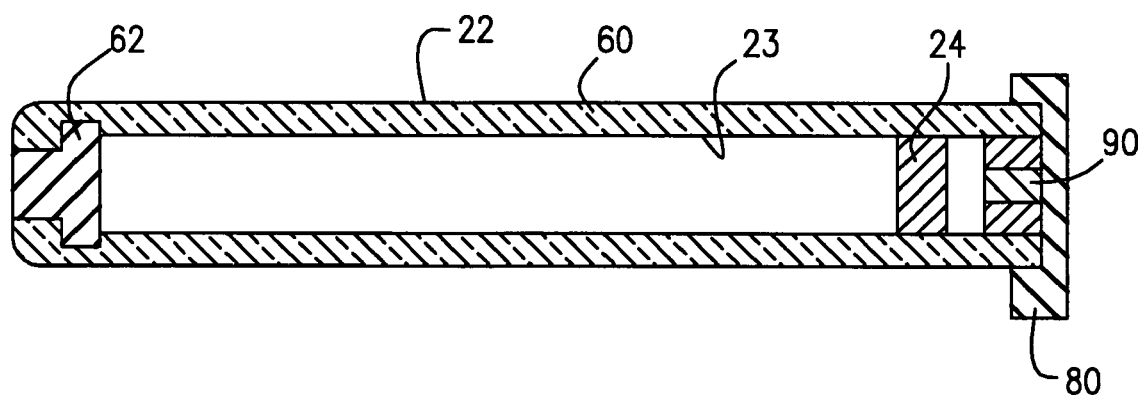
FIG. 6 is a cross-sectional side view of an exemplary cartridge of FIG. 1 having yet another appearance in accordance with some aspects of the invention.

In yet another embodiment, FIG. 6 where like reference numerals refer to like structures a cartridge 22 is illustrated with a cap 80 covering an opening filled with a membrane material 90 that is selected with application specific features. The membrane 90 can provide one-way withdrawal or inhalation of ambient air. Where this configuration is used for the storage of a drug the membrane can operate once the piston 24 is pulled away to allow air into the chamber 23, but would otherwise prevent air from entering while the piston remains in contact with the membrane. Such a membrane of this type may be a rubber stopper and flap forming a bellows valve or the like. Furthermore, the membrane may be adapted to allow for the passage of only certain gases and in certain directions to address thermal changes or other factors during storage while reducing contamination with ambient air.

With the benefits of a piston-less syringe and cartridges usable for the long term storage of drugs and an improved delivery device that can be easily adapted ergonomically for different applications and without reliance on electrical or battery power for use, the savings to the medical community in manufacture, storage and transportation of drugs and drug delivery devices may be fully realized by understanding that ampoules or vials are now conventionally delivered with disposable syringes at any facility supplying injections. The syringe and ampoule are manufactured under sterile conditions and must be transported and stored at the local facility increasing storage costs, transportation and manufacturing costs. By using a cartridge as the drug storage vehicle as it is designed to handle long term storage or storage periods that make better economic sense and are consistent with logistical and strategic purchasing strategies, the ampoule is eliminated from transport and storage. The cartridges are more compact and can be stored more efficiently. Transfer devices such as needles can be stored with the cartridges rather than requiring the storage of entire syringes. Various reusable delivery devices can be stored in limited numbers on site, substantially reducing the storage space now used for disposable syringes. Cartridges can be used in other dosing devices decreasing the need for specialized drug dispensing equipment. The improved seal of the cartridges allows for the contemplation of gaseous medical material to be stored in the cartridge, which was not possible in conventional cartridge designs. Also the bi-directional movement of the piston allows for powders to be stored and used in the cartridge in which a liquid is drawn into the cartridge at the time of use to reconstitute the powder for injection in a liquid form. Thus, utilizing a system in which:

1. A trigger mechanism that uses magnets and magnetic energy to inject and withdraw eliminating plunger mechanism is provided.

2. All dosages come in a completely sealed cartridges placed into a trigger mechanism. These have a shelf life limited only by the stability of the drug and could be estimated in for storage periods believed to be similar to ampoules or vials.

3. This cartridge forms a syringe and a storage vessel at the same time, as ampoules and vials are eliminated.

4. This cartridge can operate to store liquid, gas and powder.

As a Result:

1. The process increases shelf life of the drug and decreases storage space.

2. The costs of injection are reduced by eliminating ampoules, vials, syringes, pre-filled syringes, short shelf life cartridges, simplification of the drug manufacturing process, reduction in the FDA controlled inspection steps, less packaging, shipping and handling.

3. A small, compact and easy to use design and construction is provided.

4. The trigger mechanism and the cartridge are light weight and can be used for liquid, gas and powder drugs and chemicals.

5. This device works in both directions and, therefore, is capable of incretion and extraction.

6. This product when widely adapted in a facility will standardize inventory even more reducing the unnecessary varieties of syringes and cutting the cost of injection even further.

7. Pre-measured doses reduce human error and increase compliance during injection.

8. Using cartridges in different pre-measured quantities and reusable delivery devices reduces the waste of drugs and materials;

9. Shipping, storage, disposal and logistics are simplified and reduced.

It will be appreciated by those skilled in the art that the benefits and features of a magnetically actuated piston that allows for varying placement of the actuator may be used in syringe type device with or without a removable cartridge.

Furthermore, it will be appreciated the removable cartridges while described for use in a manual syringe type device may used in any type of device including computer controlled automated dispensing and sampling systems.

While the exemplary embodiment utilizes a natural magnet design, the magnet assembly may include electromagnetic solenoids for providing the magnetic actuation of the piston by an electrical switch.

It will be apparent to those skilled in the art that various modifications and variations can be made to the container and method of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A syringe comprising:
   walls forming a cylindrical chamber;
   a transfer device connected to at least one of said walls;
   a piston operating in said cylindrical chamber to transfer material between said transfer device and said cylindrical chamber;
   an actuator magnetically coupled to said piston through at least one of said walls;
   said actuator being located in a position on said syringe independent of a position of said piston;
   said cylindrical chamber being a removable cartridge having at least one opening;
   a stopper positioned in sealing engagement to said chamber to block the at least one opening and penetrable by said transfer device;
   a removable portion of said chamber that creates a second opening positioned relative to said piston and said stopper when removed, said second opening permitting air transfer through said chamber when said piston moves between said stopper and said second opening, and
   wherein said cartridge is connected to said transfer device and said piston transfers material between said transfer device and said cylindrical chamber.

2. A medical material storage and delivery cartridge comprising:
   a casing forming a cylindrical chamber having at least one opening;
   a stopper positioned in a sealing engagement to said casing to block the at least one opening and penetrable by a transfer device;
   a piston operating in said cylindrical chamber such that when said cartridge is connected to the transfer device, said piston transfers material between the transfer device and said cylindrical chamber, and
   wherein said cartridge includes a removable portion of said casing that when said portion is removed creates a second opening positioned relative to said piston and said stopper to permit air transfer through said casing when said piston moves between said stopper and said second opening.

3. The cartridge of claim 2 wherein said piston is magnetically responsive to operate without a mechanical linkage to a piston rod.

4. A medical material storage and delivery cartridge comprising:
   a casing forming a cylindrical chamber having at least one opening;
   a stopper positioned in a sealing engagement to said casing to block the at least one opening and penetrable by a transfer device;
   a piston operating in said cylindrical chamber such that when said cartridge is connected to the transfer device, said piston transfers material between said transfer device and said cylindrical chamber;
   a second opening in said casing positioned relative to said piston and said stopper to permit air transfer through said casing when said piston moves between said stopper and said second opening, and
   a removable cap sealingly engaged to said casing to cover said second opening.

5. The cartridge of claim 4 further including a membrane in said second opening operating to limit the transfer of air through said casing.

6. The cartridge of claim 5 wherein said membrane limits the direction of the transfer of air.

7. The cartridge of claim 4 wherein said piston is magnetically responsive to operate without a mechanical linkage to a piston rod.

8. A method for storing and dispensing medical material comprising the steps of:
   providing a cartridge including a casing forming a cylindrical chamber having at least one opening, a stopper positioned in a sealing engagement to said casing to block the at least one opening and penetrable by a transfer device, and a rodless piston;
   inserting a medical material into said cartridge;
   storing said medical material in said cartridge;
   creating a second opening in said cartridge, and
   dispensing said medical material from said cartridge to a living body by operating said rodless piston in said cylindrical chamber such that when said cartridge is connected to the transfer device said rodless piston transfers material through said transfer device from said cylindrical chamber to the living body.

9. A method for storing and dispensing medical material comprising the steps of:
   providing a cartridge including a casing forming a cylindrical chamber having at least one opening, a stopper positioned in a sealing engagement to said casing to block the at least one opening and penetrable by a transfer device, and a rodless piston;
   inserting a medical material into said cartridge;
   storing said medical material in said cartridge;
   creating a second opening in said cartridge;
   dispensing said medical material from said cartridge to a living body by operating said rodless piston in said cylindrical chamber such that when said cartridge is connected to the transfer device said rodless piston transfers material through said transfer device from said cylindrical chamber to the living body, said dispensing step also including the steps of attaching said cartridge to a delivery device and moving said rodless piston to operate in said chamber by a magnetic coupling to an actuator of said delivery device, and
   wherein said rodless piston transferring material through said transfer device from said cylindrical chamber to the living body and said storing step are order independent.

* * * * *